United States Patent [19]

Hawkins, Jr.

[11] 4,230,123
[45] Oct. 28, 1980

[54] NEEDLE SHEATH COMPLEX AND PROCESS FOR DECOMPRESSION AND BIOPSY

[76] Inventor: Irvin F. Hawkins, Jr., Mail Dept. Radiology Shands Teaching Hospital, Gainesville, Fla. 32601

[21] Appl. No.: 956,404

[22] Filed: Oct. 31, 1978

[51] Int. Cl.³ .................. A61B 6/00; A61B 10/00
[52] U.S. Cl. ................... 128/658; 128/753; 128/754; 128/772; 128/350 R
[58] Field of Search ................. 128/751–755, 128/310, 329, 350, 214.4, 654–658, 772

[56] References Cited
U.S. PATENT DOCUMENTS

| | | | |
|---|---|---|---|
| 2,496,111 | 1/1950 | Turkel | 128/754 |
| 2,850,007 | 9/1958 | Lingley | 128/754 |
| 2,919,692 | 1/1960 | Ackermann | 128/754 |
| 3,500,828 | 3/1970 | Podhora | 128/214.4 |
| 3,809,081 | 5/1974 | Loveless | 128/214.4 |
| 3,941,119 | 3/1976 | Corrales | 128/657 |
| 3,993,079 | 11/1976 | Gatztañondo | 128/214.4 |

*Primary Examiner*—Kyle L. Howell
*Attorney, Agent, or Firm*—Anthony T. LoPucki

[57] ABSTRACT

A needle sheath complex and related process for external use of the complex for decompressing or sampling tissue within a multitude of areas in human and animal bodies.

The needle sheath complex is comprised of a small gauge needle which is comprised of a stylus within a cannula and which is long enough so that a shorter outer sheath can be slidable located on the small gauge needle leaving exposed a long enough portion of the smaller gauge needle to probe the body and locate the area to be decompressed or sampled. The small gauge needle is inserted into the body and when the target area has been located, the outer sheath is slid over the small gauge needle into the body stretching the opening to the target. The smaller needle is then removed leaving the larger inside diameter sheath in place in the body through which sampling or decompression can be performed. The invention includes means and processes for easily removing and reinserting the stylus within the cannula and means and processes for readily attaching or detaching the stylus from the cannula.

The invention includes means for locking the cannula of the small gauge needle to the stylus thereby freeing both hands for guiding the small gauge needle to the target.

A key feature is the removable means for locking the probe cannula to the stylus which enables changing the outer sheath without removal of the probe cannula or stylus from the target area.

5 Claims, 6 Drawing Figures

FIG. 1
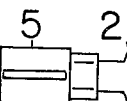
FIG. 2
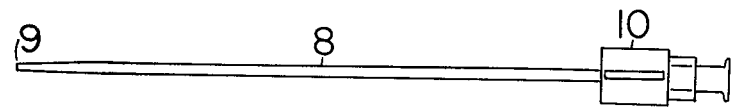
FIG. 3
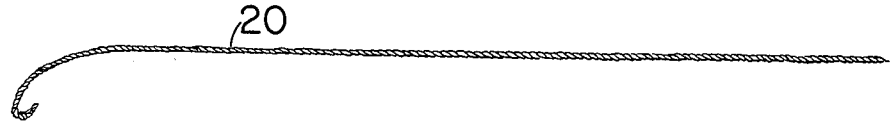
FIG. 4
FIG. 5
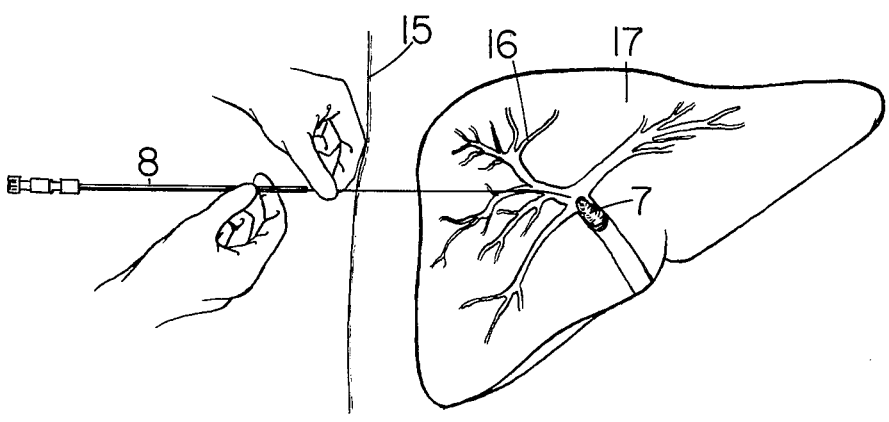
FIG. 6

NEEDLE SHEATH COMPLEX AND PROCESS FOR DECOMPRESSION AND BIOPSY

BACKGROUND OF THE INVENTION

1. Field of Invention

The invention involves a needle sheath complex and related process for performing biopsies, decompressions and similar operations at most locations within human and animal bodies without opening the body or doing substantial damage to the structures of the body. The location of the area and structures within the body to be decompressed, sampled or treated in various ways is located by insertion of a relatively small needle which enables location and verification of location. Before removal the needle, is used as a guide over which a large sheath is slid into place stretching the opening along the needle to drain the area or take the sample etc. The subject device and process have virtually unlimited applications for locating and then gaining access to virtually any part of the human or veterinary anatomy including for example the brain, ventricular system, cystic masses, liver, biliary tree, and kidneys.

2. Description of the Prior Art

The use of a small needle (22 to 23 gauge) to locate tumors, or normal structure such as a kidney or an artery has become routine in the last several years because this gauge needle can pass through most of the human anatomy without doing significant damage. However, a needle this size is to small to permit adequate drainage for therapeutic purposes (decompression of the biliary tree or urinary tract, etc.) and it is too small to extract samples of infected material or suspect structure for diagnostic purposes. The small needle captures only cells which at times is not adequate for a definitive diagnosis. Accordingly, a larger needle (15 to 18 gauge) is required to do these jobs. The larger size can be extremely dangerous if multiple passes are required and where arteries or other sensitive structures may be punctured sufficiently to cause internal bleeding or malfunction. A second entry with a larger needle which may again require multiple attempts presents a risk that the present invention can minimize while offering a multitude of advantages and capabilities previously unavailable.

SUMMARY OF THE INVENTION

The subject invention makes possible a simultaneous employment of both systems (the small needle and larger needle). In both the prior art and the present invention, the small gauge needle involved is comprised of a stylus (solid sharp wire) which slides into and fills a tubular needle, called a cannula, the outside diameter of which is referred to as the gauge size of the needle. The cannula, if relatively rigid metal with a sharp cutting end is called a biopsy needle.

The present invention utilizes a longer than normal small gauge needle hereinafter referred to as the probe cannula which can include a stylus with a shorter larger gauge sheath which fits over the small gauge needle. If the outer sheath is soft, it is often called and is generally used as a catheter for decompressing areas filled with fluids; if the outer sheath is rigid it is called a cannula or punch biopsy needle. Both the probe cannula and catheter or biopsy needle can have fittings on one end of the device so that a syringe or other equipment can be easily connected.

The probe cannula is then used to penetrate the body and locate the target area. A fluoroscope can be used to direct the probe cannula to the target and the position and structure verified by injecting a radiopaque dye through the probe cannula and applying normal radiological methods. If the target has been missed, the small needle can be backed out for another pass. When the target is located, without removing the probe cannula, the larger sheath can be slid over the probe cannula to the target. The probe cannula is then removed and a syringe can be attached to the outer sheath to apply suction to remove a tissue sample or to decompress the area. The biopsy needle or catheter (outer sheath) has only made one pass and the risk of inadvertently hitting a sensitive organ or artery with the larger outer sheath has been vastly reduced.

A feature of the invention is that it includes means for locking the outer sheath of the probe cannula to the stylus so that in the locked position both hands are free to direct the probe cannula to the target. When the probe cannula is in place, the stylus can be unlocked and removed. The locking mechanism also incorporates a fitting on the probe cannula to which a syringe or other devices can be readily attached during the procedure. The entire fitting is removable which gives the further capability of removing the larger outer sheath and if desireable exchanging it for one of a different size or rigidity or with a different fitting on it.

An apparent advantage to the invention and related procedure is that decompression or biopsy has become possible with one guided pass of the larger yet minimal biopsy needle or catheter to the target which can be accomplished without removing the smaller needle.

Another key advantage is the capacity and flexibility offered by the locking means for the probe cannula and stylus which locks one element to the other, enables ready connection of equipment, and can be removed entirely to exchange the outer sheath without removal of the probe cannula and interruption of the overall procedure.

Other inherent advantages of the invention will be apparent to those skilled in the art by reference to the following description and reference to the drawing.

BRIEF DESCRIPTION OF THE DRAWINGS

FIG. 1 shows the stylus which is the cutting element in the probe cannula with attached hub.

FIG. 2 shows the outer tubular needle of the probe cannula with removable lock and syringe fitting.

FIG. 3 shows the outer sheath (biopsy needle or catheter) with a fitting.

FIG. 4 shows a cross section of the entire assembled needle sheath complex.

FIG. 5 shows the J guide wire which can be passed through the probe sheath.

FIG. 6 shows a schematic cross section through a human body demonstrating the insertion of the invention into the liver and held in place within the main biliary tree of the liver with the outer sheath biopsy needle in position to be inserted over the probe cannula to biopsy a growth within or decompress the organ.

DESCRIPTION OF THE PREFERRED EMBODIMENT OF THE INVENTION

In FIG. 1, a solid stylus 1 is shown of the type commonly used in a cannula needle which is the combination of the stylus 1 and the probe cannula 2 shown in FIG. 2. The preferred embodiment of the invention as partially shown in FIG. 1 includes a cap 3 on one end of the stylus 1 which facilitates a grip on the stylus and provides means for locking the stylus to the probe cannula 2. At the opposite end of the stylus 1 is a sharp piercing end 4.

The stylus 1 fits within and fills the probe cannula 2 with the sharp piercing end 4 of the stylus 1 projecting slightly beyond the probe cannula 2 to enable the combination to pierce the body structure through which the combination is past. On the end of the probe cannula 2 opposite from the piercing end a lock fitting 5 is attached for connecting the probe cannula 2 to a syringe or other devices. The throat 6 FIG. 4 of the lock-fitting 5 is funnel shaped to facilitate the insertion of the stylus 1 or other fine wire such as the J-guide wire 20 into the probe cannula 2 during use of the invention.

The hub 3 on the stylus 1 is threaded to connect it to the lock fitting 5 to fix the stylus 1 to the probe cannula 2 during insertion into the body, thereby freeing both hands to more carefully guide the probe cannula 2 to the target 7 as schematically shown in FIG. 6.

The outer sheath 8 (generally a biopsy needle or catheter) as shown in FIG. 3 is shorter than the length of the probe cannula 2 and has an inside diameter large enough to decompress a cavity in a human or veterinary body of most fluids and also to withdraw by punch-cut, suction, grinding or insertion of devices through the interior of the outer sheath 8 a tissue sample adequate for diagnoses. The outer sheath 8 can be any length as long as the probe cannula 2 is longer than the outer sheath 8 by the depth of the target 7 in the body 15. The inventor has had the best results using a 15 to 18 gauge outer sheath 8 over a 22 to 23 gauge probe cannula 2. FIG. 3 shows that the end of the outer sheath 8 closest to the sharp piercing end 4 of the stylus 1 has a smooth taper 9 from its outer diameter measured at its midpoint to a snug fit against the outer diameter of the probe cannula 2 at that end of the outer sheath 8. The smooth taper 9 enables the user to slide the outer sheath 8 along the probe cannula 2 through the body structure to the target 7 with minimal damage while making available for various procedures the larger interior diameter of the outer sheath 8 through which to work.

At the end of the outer sheath 8 opposite taper 9 is a common syringe fitting 10 which enables attachment of a syringe or pump to the outer sheath 8 when desired. The syringe fitting 10 has a funnel-shaped throat 11 which facilitates insertion of smaller diameter tubes into the outer sheath when that is desired by the user. The user may insert the J guide wire 20 to hold the outer sheath (catheter) 8 in place during a draining procedure.

FIG. 4 shows a cross-sectional view of the assembled invention. This view shows in greater detail lock-fitting 5 on the probe cannula 2 which enables locking of the stylus 1 and cap 3 to the probe sheath 2 by a female course thread interacting with the lip 21 of the lock-fitting 5. The lock fitting 5 also enables connection of a syringe to the probe cannula 2 so that dye (radiopaque) can be injected to a suspected target to verify the location of the probe cannula 2. The lock fitting 5 is comprised of female threaded sleeve 12 which squeezes a rubber O-ring 13 against a male sleeve 14 thereby sealing the lock fitting 5 against the probe cannula 2.

The user of the invention has the flexibility available in sampling, decompressing or other procedures of unscrewing sleeves 12 and 13 and removing lock fitting 5 to permit the exchange of a biopsy cannula 8 for a catheter 8 or to change the size of either without removing the probe cannula 2 from the body 15.

The invention enables the user to insert the smaller diameter probe cannula 2 into a body 15 as shown in FIG. 6 toward a target growth for example shown in the biliary tree 16 within the liver 17. The relatively small probe sheath can be advanced with both hands (which are free due to the locking feature of the cap 3 and lock fitting 5) to the target site 7.

When the probe cannula 2 is at the suspected target 7, the next step is to remove the stylus 1 to see if there is an indication of the location by the nature of the fluid received through the probe cannula 2. The following step could be the connection of a syringe to the probe cannula 2 to inject radiopaque so that the location and structure at the tip of the probe cannula 2 can be verified.

A J guide wire 20 shown in FIG. 5 can be inserted through the probe cannula 2 after removal of the syringe. The J guide wire 20 helps to stabilize the location of the tip of the probe cannula 2 within the cavity (biliary tree 16) within the liver 17.

If it is desired to take a tissue sample of the target 7, the biopsy needle 8 would be advanced along the probe cannula 2 until its end was at the tip of the probe cannula 2 and against the target.

Using the invention and related process, only one puncture of the liver 17 and biliary tree 16 by the larger biopsy needle 8 has been necessary and it has been as gently performed as practical by stretching the hole created by the probe cannula 2 by means of the taper 9 between the midpoint and end of the outer sheath 8. The next step is to pull the J guide wire out and then remove the probe cannula 2. The sample could be removed by a number of techniques such as advancing the cutting tip of the outer sheath 8 into the target 7 and sucking the sample into the biopsy needle 8 by attaching a syringe to the syringe fitting 10. The sample thus obtained is generally large enough to obtain a definitive diagnosis this method of entry into the body can be used for a wide variety of procedures such as the insertion of prosthetic devices by using progressively larger outer sheaths 8 opening a pathway to the target site.

Another feature of the needle sheath complex is that marks 19 can be added to the probe cannula 2 to gauge when the tip of the outer sheath is at the tip of the probe cannula.

As can be seen by contemplation of the above procedure using the needle sheath complex, the same operation can be of use in nearly all structures of the body whenever there is need to decompress an area from an undesirable accumulation of fluid, take a biopsy sample, structure sample or even to withdraw an unwanted mass from an organ.

Normal luminal structures such as the circulatory system can be opacified with a similar process even though a small gauge needle is generally not large enough to supply dye at a flow rate adequate for diagnostic studies as the normal flow of body fluids carries the dye away too quickly. The larger outer sheath 8 solves this problem without need for multiple passes of the larger outer sheath 8 into the body's structures.

Some of the contemplated uses in various organs for opacification of normal structures, biopsy, drainage or insertion of therapeutic devices include; the brain (ventriculography, diagnosis and drainage of cystic masses and solid masses); chest (drainage), lung (diagnosis and biopsy of cyst abscesses, tumors, pleural effusions, pericardial cysts and pericardiocentensis; liver (biliary tree portography, abscesses, cyst punctures stent placement and embolization of collateral portal veins); Pancreas (tumors, cysts, pseudocysts); stomach (masses); kidney (antegrade pyelography, cyst punctures, biopsy of masses, stent placement for obstructed urinary tract); Ovaries (drainage and diagnosis of ovarian cysts, tumors, etc.); Peritoneal cavity (biopsy and tube placement, peritoneal dialysis catheter placement); uterus (diagnostic punctures, biopsies, etc., amniocentensis, fetal transfusions, etc.); Extremities (drainage of abscesses, cysts, biopsy of masses, etc.).

The embodiment described illustrates the features of the invention in a form which the inventor has found most practical and suited to his uses; however, other configurations can be generated by persons reasonably skilled in the art which would practice the novel features of the invention. Such variations are considered to be within the spirit and scope of the invention and are claimed as stated below.

For example the subject device and procedure can be used to insert prosthetic devices after opening a pathway to the site.

I claim:

1. A needle sheath complex for use in locating, removing matter from, and inserting devices in human bodies and animal bodies consisting of:
   a. a probe cannula of tubular shape and consistent diameter having a small enough outer diameter to penetrate sensitive organs, arteries, and other body structures without doing substantial damage;
   b. a stylus slidably located within said probe cannula with a diameter which fills said probe cannula, said stylus having a sharp piercing end and being enough longer than said probe cannula to project slightly from the end of said probe cannula to provide a cutting end;
   c. an outer sheath of tubular shape slidably located over said probe cannula having an inside diameter large enough to remove matter from or insert devices in said bodies, said outer sheath being long enough to extend from the target in the body to the outside of the body and said probe cannula being at least twice that length;
   d. Means for locking said stylus within said probe cannula in position, said means being removable from said probe cannula so that said outer sheath may be removed from said probe cannula whereby said outer sheath may be replaced with an outer sheath which is more rigid, less rigid, or larger in diameter, or capable of procedures different from the outer sheath removed without removing said probe cannula from the body.

2. The needle sheath complex claimed in claim 1 wherein said means for locking said stylus within said probe cannula is comprised of a lock fitting attached to an end of said probe cannula which enables attachment of a syringe or other devices to said probe cannula and a hub attached to said stylus having means for detachably connecting said hub to said lock fitting.

3. The needle sheath complex claimed in claim 2 wherein said outer sheath includes detachable means for attaching a syringe to the end of said outer sheath.

4. The needle sheath complex claimed in claim 1 wherein the end of said outer sheath which is closest to said sharp piercing end of said stylus being tapered smoothly from its outside diameter down to a snug but slideable fit between the outer diameter of said probe cannula and the inside diameter of said outer sheath so that when the outer sheath is slid into the body over the probe cannula the opening is stretched to the larger diameter.

5. A process for locating a specific target within a human or animal body, verifying that the target has been located, decompressing the cavity by catheterization and sampling the target cavity structure with a biopsy needle consisting of the following steps:
   a. Inserting a small diameter probe cannula have a stylus which fills the probe cannula and which is enough longer than the probe cannula so that a sharp end of the stylus projects from the probe cannula and wherein said stylus is detachably fastened to said probe cannula so that both hands are free to guide the probe cannula to the target cavity within said body;
   b. Detaching said stylus from said probe cannula and removing it;
   c. Attaching a syringe to said probe cannula to draw a sample of fluid to determine whether the fluid will identify the target;
   d. Sliding a catheter over said probe cannula and advancing it to the target site;
   e. Removing said probe cannula from said catheter;
   f. Attaching means for draining fluid from the target area to said catheter and decompressing the area;
   g. Reinserting the probe cannula into said catheter to the target area and withdrawing said catheter;
   h. Sliding a biopsy needle over said probe cannula and advancing said outer sheath to the target area; and
   i. Taking a biopsy sample through said biopsy needle.

* * * * *